United States Patent
Spahn et al.

(10) Patent No.: US 11,096,759 B2
(45) Date of Patent: Aug. 24, 2021

(54) OPERATING A MEDICAL IMAGE RECORDING DEVICE

(71) Applicant: Siemens Healthcare GmbH, Erlangen (DE)

(72) Inventors: Martin Spahn, Erlangen (DE); Philipp Bernhardt, Forchheim (DE); Stefan Böhm, Oberasbach (DE); Boris Stowasser, Erlangen (DE); Richard Obler, Erlangen (DE); Stanislav Tashenov, Heroldsbach (DE); Rudolf Leiblein, Weisendorf (DE); Andreas Berting, Schlüchtern (DE); Markus Lendl, Ottensoos (DE); Oliver Baruth, Herzogenaurach (DE)

(73) Assignee: Siemens Healthcare GmbH, Erlangen (DE)

( * ) Notice: Subject to any disclaimer, the term of this patent is extended or adjusted under 35 U.S.C. 154(b) by 60 days.

(21) Appl. No.: 16/442,492

(22) Filed: Jun. 15, 2019

(65) Prior Publication Data
US 2019/0380806 A1     Dec. 19, 2019

(30) Foreign Application Priority Data
Jun. 15, 2018   (EP) .................................... 18178021

(51) Int. Cl.
*G06T 7/32* (2017.01)
*A61B 90/00* (2016.01)
(Continued)

(52) U.S. Cl.
CPC .............. *A61B 90/36* (2016.02); *A61B 6/032* (2013.01); *A61B 6/5229* (2013.01); *A61B 6/547* (2013.01);
(Continued)

(58) Field of Classification Search
CPC ......... A61B 90/36; A61B 34/20; A61B 6/032; A61B 6/5229; A61B 6/547;
(Continued)

(56) References Cited

U.S. PATENT DOCUMENTS

| | | |
|---|---|---|
| 2009/0310741 A1 | 12/2009 | Borghese |
| 2010/0312094 A1 | 12/2010 | Guttman |

(Continued)

FOREIGN PATENT DOCUMENTS

| | | |
|---|---|---|
| EP | 2130491 A1 | 12/2009 |
| JP | 2014144118 A | 8/2014 |

(Continued)

OTHER PUBLICATIONS

European Office Action for European Patent Application No. 18178021.4-1126, dated Nov. 28, 2018.
(Continued)

*Primary Examiner* — Chuong A Ngo
(74) *Attorney, Agent, or Firm* — Lempia Summerfield Katz LLC

(57) ABSTRACT

Operating a medical image recording device in the context of an image recording routine for a patient is provided. The image recording routine serves an image recording purpose. The image recording device is controlled based on operating parameters implemented by a controller of the image recording device. The operating parameters are identified completely automatically by an identification algorithm from input data describing at least the patient in the form of a patient model and/or the image recording purpose, and from a registration of the patient with a coordinates system of the image recording device. The operating parameters are used to control the image recording device. An examination region that is to be recorded for the patient and the image recording purpose are derived based on the registration.

19 Claims, 2 Drawing Sheets

(51) Int. Cl.
*A61B 34/20* (2016.01)
*A61B 6/03* (2006.01)
*A61B 6/00* (2006.01)
*A61N 5/10* (2006.01)
*G06T 7/38* (2017.01)
*G16H 50/50* (2018.01)
*G16H 30/40* (2018.01)
*G06N 3/08* (2006.01)

(52) U.S. Cl.
CPC ............ *A61B 34/20* (2016.02); *A61N 5/1049* (2013.01); *G06T 7/32* (2017.01); *A61B 6/5217* (2013.01); *A61B 2034/2055* (2016.02); *A61B 2090/364* (2016.02); *A61N 2005/1059* (2013.01); *G06N 3/08* (2013.01); *G06T 7/38* (2017.01); *G16H 30/40* (2018.01); *G16H 50/50* (2018.01)

(58) Field of Classification Search
CPC ...... A61B 2034/2055; A61B 2090/364; A61B 6/5217; A61B 6/545; A61B 6/467; A61B 6/5294; A61B 6/00; A61B 6/08; G06T 7/32; G06T 7/38; A61N 5/1049; A61N 2005/1059; G06N 3/08; G16H 40/63; G16H 50/50; G16H 30/40
See application file for complete search history.

(56) References Cited

U.S. PATENT DOCUMENTS

| | | |
|---|---|---|
| 2012/0148131 A1 | 6/2012 | Couch |
| 2012/0209093 A1* | 8/2012 | Olszewski .......... A61B 6/5217 |
| | | 600/310 |
| 2017/0135654 A1 | 5/2017 | Van Daal |
| 2017/0340902 A1 | 11/2017 | Vilsmeier |
| 2018/0103912 A1 | 4/2018 | Canfield |
| 2018/0140260 A1 | 5/2018 | Taguchi |
| 2018/0157800 A1 | 6/2018 | Ravishankar |
| 2020/0051699 A1 | 2/2020 | Tahmasebi Maraghoosh |

FOREIGN PATENT DOCUMENTS

| | | |
|---|---|---|
| JP | 2017522943 A | 8/2017 |
| JP | 2018082767 A | 5/2018 |
| WO | WO2018048507 A1 | 3/2018 |
| WO | 2018069201 A1 | 4/2018 |

OTHER PUBLICATIONS

Japanese Office Action for Japanese Application No. 2019-094471 dispatched Sep. 29, 2020, with English translation.

* cited by examiner

OPERATING A MEDICAL IMAGE RECORDING DEVICE

This application claims the benefit of EP 18178021.4, filed on Jun. 15, 2018, which is hereby incorporated by reference in its entirety.

BACKGROUND

The present embodiments relate to operating a medical image recording device in the context of an image recording routine for a patient.

Modern medical image recording devices are complex systems for which operation represents a considerable challenge to users required to obtain suitable or even optimal image quality during an image recording routine for a patient. It is therefore customary in the prior art for users to be offered a choice of manually selectable predefined measurement protocols, so that users may select an appropriate measurement protocol based on the image recording purpose of the current image recording routine. Such measurement protocols are also referred to as "organ programs" (e.g., when X-ray devices are used as image recording devices).

The measurement protocols, which define operating parameters that are to be implemented by a control device of the image recording device, are extremely varied in this case, as are the possible image recording purposes and medical disciplines. For example, measurement protocols may be provided both for various diagnostic examinations and for interventions in the field of cardioangiography, electrophysiology, neurointervention, general angiography, pediatrics, surgery, etc. relating to different organs (e.g., heart, liver, head, legs, spinal region, etc.). The measurement protocols differ with respect to operating parameters (e.g., physical operating parameters such as dose, tube voltage, pulse length, image frequency, detector resolution, detector mode, tube focus, etc. in the case of X-ray devices, and/or evaluation-related operating parameters such as native mode, subtraction mode, general image overlay (fluoroscopy and 3D image data sets), type and manner of image-based or temporal noise suppression, frequency-dependent contrast increase and/or decrease, management of the image dynamics, image sharpness, etc.). On an image recording device having a growing number of potential uses and areas of use, provision may be made for an ever increasing number of optimized measurement protocols offering suitable operating parameters, both image recording parameters and image evaluation parameters.

For the purpose of a respective image recording routine, which may also be an examination stage and/or a treatment stage (e.g., a diagnostic part of a treatment routine, positioning of a medical instrument such as a balloon, stent, coil, catheter for the ablation of embolization materials or for the dosage of chemotherapeutic materials, biopsy needles, etc.), the user (e.g., a doctor) performing the diagnosis/therapy selects a corresponding measurement protocol which the doctor considers to be suitable.

It may often occur in everyday practice that the optimal measurement protocol for the image recording routine (e.g., an organ program) is not used (e.g., because the doctor as a user is focusing and concentrating on the examination/therapy and the patient or, in spite of the doctor's training, is not aware that an alternative measurement protocol may deliver better image recording results. In order to improve this situation, it has already been proposed to combine measurement protocols into a series for a complete examination or a complete treatment and thus to provide a defined sequence of measurement protocols for various examination stages or treatment stages. However, such a combination of measurement protocols does not solve the problem of the large number of measurement protocols available for manual selection.

The document US 2018/0157800 A1 discloses a method based on machine learning for providing patient-specific measurement protocols. The document WO 2018/048507 A1 discloses a method for generating a synthetic image by a neural network. In addition, the document EP 2130491 A1 discloses a patient-specific adaptation of imaging parameters by anatomy recognition. The document US 2017/0340902 A1 discloses a method for registering individual anatomical structures in an X-ray image with a coordinates system of an overview X-ray image.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a possibility for controlling operation of an image recording device that simplifies the operation of the image recording device and helps to improve image recording quality is provided.

According to an embodiment of a method for operating a medical image recording device, operating parameters are identified completely automatically by an identification algorithm from input data describing at least a patient in the form of a patient model and/or the image recording purpose, and from a registration of the patient with a coordinates system of the image recording device. The operating parameters are used to control the image recording device. An examination region that is to be recorded for the patient and the image recording purpose are derived based on the registration.

This represents a radical departure from the known prior art, which provides various measurement protocols that are manually selected, in that no measurement protocols whatsoever are now defined in the image recording device, whether selected purely manually or with assistance from the system. Instead, the physical operating parameters and image processing operating parameters that are optimal for the respective image recording routine (e.g., an examination and/or treatment phase) are directly influenced with the aid of a system-inherent intelligence in accordance with the identification algorithm. In other words, one or more of the present embodiments provide that a correspondingly qualified identification algorithm undertakes large parts or even all of the image-specific parameterization. Therefore, the user interaction in the form of, for example, a choice of measurement protocol is minimized or excluded completely.

Such an identification algorithm, which may be selected to include artificial intelligence in one exemplary embodiment, in this case utilizes, for example, input data describing the patient in the form of a patient model and an existing registration of the patient with a coordinates system of the image recording device. This provides that the location of the patient model relative to the image recording device is also known based on the registration, and therefore, it is possible, for example, to infer which examination region is to be recorded. This gives a clear indication of the image recording purpose. For example, the examination region of the patient may be identified as a result of the registration of the patient with the coordinates system of the image recording device. The image recording purpose may be derived based on the registration of the patient with the coordinates system of the image recording device and/or with the aid of the patient model. The image recording purpose may, for example, include a medical examination purpose (e.g., a combination of an image recording routine, using a further image recording modality, and/or performance of an examination and/or a treatment such as a catheter examination). The automatic determination of the image recording purpose may be advantageous, for example, for a planning schedule of the image recording routine.

With regard to the image recording purpose, for example, further input data, as described below, may also be present, making it possible when taken together to infer as accurately as possible which operating parameters give the best imaging result for the imaging type of the image recording device. Further input parameters may in general relate to system conditions and environmental conditions (e.g., medical instruments in use and/or resources for the image recording routine). Taking into account the location of the patient and therefore the anatomical structures of the patient relative to the image recording device, or the corresponding recording arrangement of the image recording device, a continuously updatable information base is also created, and may correct operating parameters as appropriate in response to dynamically changing examination regions (e.g., when tracking a medical instrument through the body of a patient, such as a catheter that is to be guided, from the arm or the groin to the destination, these different entry points alone suggesting clearly different suitable operating parameters, which are automatically identified by the identification algorithm based on the input data and the existing registration and may be used in the control device).

In a further embodiment, a workflow is identified based on the registration of the patient with the coordinates system of the image recording device and based on the image recording purpose derived at least therefrom. The medical image recording device may be configured to perform the identified workflow semiautomatically or automatically during the image recording routine for the patient. The workflow may include information relating to a temporal sequence of different operating parameters of the image recording device for the purpose of performing the image recording routine. In one embodiment, a workflow for a complete medical examination (e.g., a heart catheter examination) may be identified based on the automatic identification of the examination region of the patient (e.g., a groin region). This workflow may include a plurality of different operating parameters and a corresponding temporal sequence during the complete image recording routine.

In the case of semiautomatic performance of the workflow identified based on the registration and the image recording purpose, one or a plurality of workflow instructions may be output to operating staff (e.g., via a display unit). The medical image recording device may also perform the workflow automatically. In this case, the image recording routine may be monitored particularly easily and intuitively by operating staff.

In one embodiment, in addition to image recording parameters (e.g., physical operating parameters), the operating parameters may also include at least one image evaluation parameter (e.g., image processing parameter). Since many (pre-)evaluation acts relating to the image recording result (e.g., the image data) are already performed within the image recording device, it is appropriate already to adapt the image processing likewise in view of the image recording purpose that is described by the input data and may therefore be derived at least therefrom, such that in this regard, likewise an improved image quality is produced without the need for corresponding manual inputs by a user. In one embodiment, the operating parameters that may be determined automatically by the identification algorithm therefore include all of the operating parameters that previously were or could be provided by measurement protocols, such that the identification algorithm is able automatically to formulate a measurement program that is individually adapted to the current image recording routine and the current patient based on the input data.

Therefore, the identification algorithm at least partly explicitly or at least partly implicitly (e.g., by artificial intelligence) uses decision criteria that evaluate the input data or intermediate data derived therefrom. In this case, an essential decision criterion for one or more of the present embodiments is the use of the information provided by the input data for identifying the organ of interest (OOI) situated in the field of view of the image recording device, in order to automatically select the optimal physical operating parameters and, for example, also the optimal image processing operating parameters on this basis.

According to an appropriate development, the identification algorithm includes at least one artificial intelligence algorithm that was trained by machine learning (e.g., by deep learning). Although artificial intelligence is not absolutely essential, it is shown to be an extremely useful tool in the context of one or more of the present embodiments, improving the overall quality of the automatically identified operating parameters. In connection with the increasing complexity of image recording devices (e.g., due to an increasing amount of equipment and/or an increasing number of setting options), artificial intelligence is suitable for extracting connections between input parameters and operating parameters, and also between operating parameters and operating parameters if applicable, and for using the connections in accordance with a corresponding learning routine to further improve the quality of the image recording result. Suitable training data is used for this purpose.

In this context, according to an embodiment, training data for the artificial intelligence algorithm is identified by logging a user activity that includes, for example, at least one individual parameter adaptation during the use of predefined measurement protocols with predefined operating parameters. This provides that, for common measurement protocols that may be adapted by a user, it is proposed to log selection and adaptation activities of users on applicable image recording devices (e.g., taking into consideration the quality of the image recording result) in order thereby to find optimization potential in these measurement protocols and achieve a clear advantage over a mere automatic selection of suitable measurement protocols. It is appropriate in this case also to identify and log the input data in parallel (e.g., the patient model), such that the output data, specifically the user settings, is assigned to the identified input data in the training data.

According to a particularly appropriate feature of the present embodiments as mentioned above, provision is made for using a patient model that describes as accurately as possible, based on the present registration and the adaptation to the current patient, which part of the patient is placed in the field of view of the image recording device. In this context, a specific embodiment provides for using at least the patient model that has been adapted to the current patient and describes the composition of the patient in a locally resolved manner as the patient data describing the patient. In this case, a patient model based on computed tomography and/or a vector-based patient model and/or a patient model that replicates the location of at least some of the organs and/or the course of blood vessels of the patient may appropriately be used as a patient model. This provides that a patient model that is based on computed tomography or is of that type and replicates all of the important organs and the vascular tree may be used, for example. Such a patient model based on computed tomography may be derived, for example, from a computed tomography recording of the patient concerned. The patient model may also be retrieved as a generic model and is particularly suitable if the image recording device is embodied as an X-ray device, since the patient model then implicitly also describes the ability of the X-ray imaging to replicate corresponding anatomical structures. However, it is also possible to use a vector-based simple patient model, which replicates the outlines of a generic patient and the location of all important organs relative to the outlines, and is adapted (e.g., by the registration) to the current patient. Therefore, the widest variety of embodiments of patient models may generally be used, where the patient model in embodiments is essentially able in conjunction with the registration to replicate at least the location of important organs relative to the image recording device or the recording arrangement thereof.

The adaptation of the patient model to the current patient, if a generic patient model is used, may be effected, for example, by other patient data, this being derived, for example, from the registration and/or from preliminary recordings and/or from other patient information (e.g., height and/or weight and/or gender). The registration may also include the adaptation of the generically specified patient model to the current patient.

Specifically, the registration may be effected using sensor data from at least one sensor directed at the patient and/or image data of the patient recorded by the image recording device and/or based on patient data retrieved from an information system and/or based on patient location data obtained from an embodiment of a patient couch of the image recording device. In a specific embodiment, a camera (e.g., a 3D camera and/or an infrared camera and/or terahertz camera, and/or an ultrasound sensor) may be used as a sensor with other embodiments also being possible. Specifically, a multiplicity of methods may therefore be used to effect a registration of the patient with a coordinates system of the image recording device. The registration is, for example, manifested specifically in a registration of the patient model that is adapted to the current patient with this coordinates system.

Initially, a camera-based optical registration, where the camera replicates the patient on the patient couch and generates a correlation of the patient outline relative to the patient couch, which, for example, also describes the location of the patient (e.g., "head first", "feet first", "supine", "prone", etc.), may be provided. The use of an infrared camera has the advantage of being able to see through any patient covering in a sterile manner. Ultrasound recognition of the location of the patient relative to the patient couch may also be provided. In the context of the registration, patient data obtained from an information system (e.g., a hospital information system (HIS) and/or a radiology information system (RIS) and/or patient data entered at the image recording device) may be made use of. The patient data from the information system may directly describe, for example, the location of the patient on the patient couch or may also describe the patient more accurately (e.g., by height, age, gender, weight, etc.). Such patient data may be used to adapt a generically specified patient model to the current patient.

Additionally or alternatively, image-based registration may also be provided (e.g., the use of a first preliminary image and/or the first recorded image data of the patient). From the image data, information may be extracted with the aid of, for example, databases and/or artificial intelligence, where organ identification is also feasible. In one embodiment, a registration may be effected based on an embodiment of the patient couch. A patient table with an integrated pressure-sensitive film that recognizes the main supporting points of the patient (e.g., head, shoulders, buttocks, calves, feet and arms) may be used, and these are correlated with the patient model for the purpose of registration.

The adaptation of the patient model (e.g., the generically specified patient model) to the current patient may take place based on registration data that is gathered during the registration, such that features of the patient contained in the patient model may be localized in the coordinates system of the image recording device. In other words, the patient registration therefore establishes a relationship between the coordinates systems of the patient model (and hence the patient) and the image recording device, where anatomical features described by the patient model may therefore be localized in relation to the image recording device (e.g., the recording arrangement thereof) in order to draw corresponding inferences in the identification algorithm.

In the context of one or more of the present embodiments, provision may be made for input data describing the image recording purpose to be retrieved from an information system and/or for the image recording purpose to be derived from other input data (e.g., from a part of the patient that is positioned within the field of view of the image recording device). The image recording purpose (e.g., target application) may be identified from, for example, entries in a hospital information system (HIS) and/or radiology information system (RIS), since corresponding information may be obtained as part of the patient registration in the information system. Corresponding inferences may be drawn from that part of the patient that is positioned in the field of view of the image recording device, which is possible via the registration of the patient model, as described in detail above. The part that is positioned in the field of view of the image recording device may also be used or analyzed for the purpose of plausibility checking.

In an embodiment, provision may be made for the input data to include at least one item of instrument data describing a medical instrument that is used for the patient during the image recording routine. Instruments (e.g., "devices") in use may not only influence the imaging of the imaging type of the image recording device itself, but, for example, may also place specific demands on the image recording as a result of imaging properties, particularly if the replication of the medical instrument itself is involved (e.g., when tracking a catheter, checking the position of an implant, etc.). Corresponding input data that describes the medical instrument is therefore useful information for the identification of the operating parameters by the identification algorithm.

Specifically, the instrument data may be identified by using an identification device that reads an information medium on the instrument and/or a packaging of the instrument and/or from instrument data in an information system and/or by evaluating image data of the image recording device showing the instrument and/or may include at least one property that is relevant for the imaging type of the image recording device. For example, provision may be made for effectively registering the medical instruments with the image recording device by a suitable identification device reading an information medium of the medical instrument (e.g., a bar code and/or an RFID chip). Additionally or alternatively, information may be queried from an information system, and/or an image-based correlation may be performed. For example, the medical instrument may be detected within image data of the image recording device by segmentation algorithms, thereby also allowing, for example, the identification of properties of the medical instrument. Accordingly, properties of the medical instruments (e.g., properties that are relevant for the imaging type of the image recording device) may be stored. For example, at least a material of the medical instrument (e.g., platinum, plastic, iron, tantalum, iodine, etc.) and/or the geometric extension in at least one dimension (e.g., 1.2 French catheter; a catheter having a diameter of 0.4 mm, stent diameter, diameter of a stent strut, etc.) may be used as properties of the medical instruments in order to adapt the operating parameters of the image recording device that are based thereon.

If it is intended to use a small catheter, for example, it may be appropriate to adapt the operating parameters with a view to improving the resolution, in addition to any optimization of operating parameters that may already be specified with respect to the deployment region of the catheter, such that, for example, different image recording parameters and/or image evaluation parameters are used if the medical instrument is located in the liver region of the patient or in the heart region of the patient. Further information relating to the target region of the medical instrument may also be relevant (e.g., embolization in the target region, etc.).

In a further embodiment, the operating parameters identified by the identification algorithm include an operating parameter of the medical instrument that is used during the image recording routine. It is thereby possible to specify, for example, an orientation and/or location of the medical instrument based on the registration. It is also possible to identify a shared workflow of the image recording device and the medical instrument, allowing particularly time-efficient and intuitive performance of the image recording routine in order to achieve the image recording purpose. In the case of a mobile image recording device, the shared workflow may allow, for example, maximally synchronized movement of the medical instrument and the image recording device. It is also possible by a corresponding instruction in the shared workflow to prevent detrimental influences from a medical instrument that is situated in the field of view of the image recording device, for example.

In the context of one or more of the present embodiments, provision is appropriately made for the positions and/or orientations of mobile components of the image recording device (e.g., mobile components of the recording arrangement and/or the patient couch) to be known, and therefore, also corresponding positions and/or orientations (e.g., poses) in the coordinates system of the image recording device. Such component information, which may also be used as input data and/or otherwise entered into the identification algorithm, may be obtained in various ways, such that, for example, the presence and/or positions/orientations of components of the image recording device may be identified from the state of actuators assigned thereto and/or by sensors assigned to the components. In contrast with the prior art, it is also possible to add further sensors, particularly in the case of components that are positioned and/or set manually. In this case, resources (e.g., filters and/or collimators and/or grids) may be treated in a similar manner to medical instruments (e.g., also detected in (initial) image data and/or registered by information media when used).

Provision is made for the input data to be updated cyclically and/or in the event of change, resulting in an adaptation of at least one of the operating parameters based on the modified input data. This provides that the described input data may be updated synchronously with the image or at least from time to time. For example, the angulation of a C-arm and/or generally the position of a patient couch may change during an image sequence in a recording routine, such that the recording conditions and/or the examination region change. A specific example of this includes the introduction of a catheter or guide wire for access (e.g., lumbar or radial), where the catheter or guide wire is pushed via the aorta (or radial artery) to the aortic arch while the patient couch is moved in a coordinated manner. The tip of the medical instrument may thus always be seen in the recorded image data set and traverses various organs/examination regions in this way. In one embodiment, the appropriate operating parameters may be dynamically determined at all times by the identification algorithm, and therefore, improved image quality may be provided for all positions of the medical instrument because the input data and the resulting operating parameters are continuously updated.

In an appropriate development, at least one property of the recording region of the patient, the property being relevant for the imaging type used in the image recording device, may be identified by the identification algorithm and used to adapt at least one operating parameter (e.g., an image evaluation parameter).

This is now explained in greater detail with reference to a specific example for an X-ray device as an image recording device. For example, the identification of the operating parameters may include an optimization of the X-ray spectrum for the image recording purpose. The existing dose control and spectral adaptation is based on a generally used mixed model of the main patient material properties, where a specific composition assumption is made, for example. With the aid of the available input data (e.g., the identification of the part of the patient in the field of view of the image recording device), the anatomy corresponding to the part also being known from the patient model, it is possible far more specifically to estimate a more realistic composition of that part of the patient situated in the field of view. The resulting expected primary and scattered radiation components may thus be optimized by suitable X-ray spectrum selection (e.g., tube voltage, prefiltering, etc.).

The input data (e.g., the patient model) may, if applicable, also describe any existing patient implants that may likewise be taken into consideration during the selection or identification of suitable operating parameters. For example, the information relating to known implants (e.g., knee, hip, etc.) may be used to optimize the X-ray spectrum and the X-ray dose in just the same way as information relating to superimposition of collimators and/or relevant filters.

For example, filters and/or collimators that are generally used, and/or positions and/or settings thereof, may therefore be identified as input data or operating parameters. Information relating to filters/collimators and to implants may also be identified image analysis of, for example, preliminary images or initially recorded image data of the patient.

Further physical operating parameters therefore image recording parameters, may also be adapted for the purpose of optimization based on the knowledge about the part of the patient in the field of view (e.g., with reference to the organ of interest (OOI). For example, based on the input data and the registration, it is possible to predict with a high degree of probability that the image recording purpose is angiography of the right-hand coronary artery or the left-hand coronary artery, and an optimized choice of the pulse length may be effected automatically as an operating parameter. In the example of the coronary arteries, it is known that the left-hand and right-hand coronary arteries exhibit distinctly different movement speeds. The right-hand coronary artery moves distinctly faster than the left-hand coronary artery here. If the information indicating which coronary artery is to be examined is known (e.g., inferred from registration, patient model, field of view of the image recording device) and optionally if the image recording purpose is known (e.g., target application—cardioangiography), it is possible to effect a corresponding adaptation of the pulse length of the X-ray pulse and/or the image frequency in the operating parameters in order to optimize the temporal resolution and avoid or reduce movement artifacts.

A further useful field of application for the described procedure includes image recording routines including multiple single image recordings that are chronologically sequential. For the individual image recording time points, it is possible (e.g., based on the registration and the patient model) to identify physical operating parameters describing the recording geometry in relation to the patient (e.g., system positions including the position of a patient couch and/or a recording arrangement (possibly including orientation in each case)). For example, after approval by an operator, the system positions are adopted one after the other, and the image recordings are made. Such a procedure is customary in the field of coronary diagnostics in the case of X-ray devices (e.g., using a C-arm). The system positions may then include the position of a patient couch and the angulation of a C-arm. In the same way as other operating parameters may be determined by an artificial intelligence algorithm, this also applies to such sequences of system positions (or recording geometries in general). Training data may be obtained during similar examinations of other patients, for example.

The optimizing determination of operating parameters is, however, not limited to physical operating parameters (e.g., image recording parameters), but may also relate to image evaluation parameters (e.g., image processing parameters). For example, depending on the physical operating parameters selected by the identification algorithm and/or information relating to the medical instruments used and/or implant information, the image processing may be optimized synchronously with the image (e.g. with respect to the strength of the temporal and image-based noise suppression, the management of contrast and dynamics, the spatial frequency-dependent image sharpness, etc.).

According to a further embodiment, the operating parameters describe the automatic output of at least one workflow instruction (e.g., relating to a resource to be used during the image recording and/or in order to minimize a negative effect on the patient). This provides that operating parameters may also relate to the interaction with a user, specifically by supporting the user when a workflow assigned to the image recording routine is performed, for example. For example, the user may receive workflow instructions relating to the corresponding output device (e.g., the type and/or positioning of a resource to be used during the image recording) and/or instructions for optimal handling of the patient during the image recording routine. The workflow instruction may enable semiautomatic performance of the image recording routine. For example, an instruction with respect to a movement direction of the image recording device and/or the patient couch may be output to operating staff during a catheter examination. Insofar as the input data includes information relating to further components of the image recording device and/or a medical instrument, detrimental influences in the image recording routine may be prevented by the output of a corresponding workflow instruction to operating staff.

For example, it may be recognized from the input data for the patient under examination whether this is a pediatric patient (e.g., a small child) or an adult. For example, this may result in a workflow instruction to use the antidiffusion grid or to remove the antidiffusion from the ray path in the case of pediatric examinations if the image recording device is embodied as an X-ray device. It is likewise extremely useful in the case of X-ray devices for workflow instructions relating to optimization of the local dose load (e.g., the skin dose) to be generated automatically at the image recording device. In this way, workflow instructions may recommend, for example, a change in recording geometries (e.g., to complementary angulations) in order to minimize the locally applied skin dose for the patient in the case of lengthy image recording routines. When using other image recording devices (e.g., a magnetic resonance device as an image recording device), such a workflow instruction may relate to the local and/or global SAR, for example.

In addition to the method, one or more of the present embodiments also relate to an image recording device (e.g., an X-ray device) having a recording arrangement and a control device (e.g., a controller) that is configured to perform a method according to one or more of the present embodiments. All of the explanations relating to the method may be transferred analogously to the image recording device, which therefore likewise offers the advantages cited above. The control device may include at least one processor and/or at least one storage device. For the purpose of performing the method, the control device may have, for example, an identification unit that implements the identification algorithm. A registration unit may also be provided for registering the patient (e.g., on the basis of the patient model) with a coordinates system of the image recording device. The control of the image recording device by implementing the operating parameters may be effected by a corresponding control unit.

A computer program according to one or more of the present embodiments may be loaded directly into a storage device of a control device of an image recording device, for example, and has a program for executing the acts of a method according to the present embodiments when the computer program is executed in the control device of the image recording device. The computer program may be stored on a data medium that is electronically readable according to one or more of the present embodiments and therefore includes electronically readable control information stored thereon. The control information includes at least such a computer program and is so configured as to perform a method according to one or more of the present embodiments when the data medium is used in a control device of an image recording device. The data medium may be a non-transient data medium (e.g., a CD-ROM).

DETAILED DESCRIPTION

Exemplary embodiments are discussed in the following with reference to an X-ray device as an image recording device. Application to other image recording devices of greater complexity (e.g., magnetic resonance devices) may also be provided.

Optimal physical and image processing operating parameters are to be selected in a fully automatic manner by a control device of the image recording device based on some or all of the available input information, such as, for example: a patient model adapted to the current patient; registration of the patient model and therefore the patient with a coordinates system of the image recording device; knowledge of the image recording purpose; information relating to a current examination region (e.g., organ of interest (OOI)); information relating to implants, direct radiation, location of filters/collimators, inclusion of expected movements in the examination region; and knowledge relating to medical instruments used or the medical instrument that is most critical for the imaging. For this purpose, use is made of a qualified identification algorithm, which may undertake all image-relevant parameterization of the image recording device, thereby removing any requirement for user action (e.g., the selection of a measurement protocol or organ program).

Figure 1:
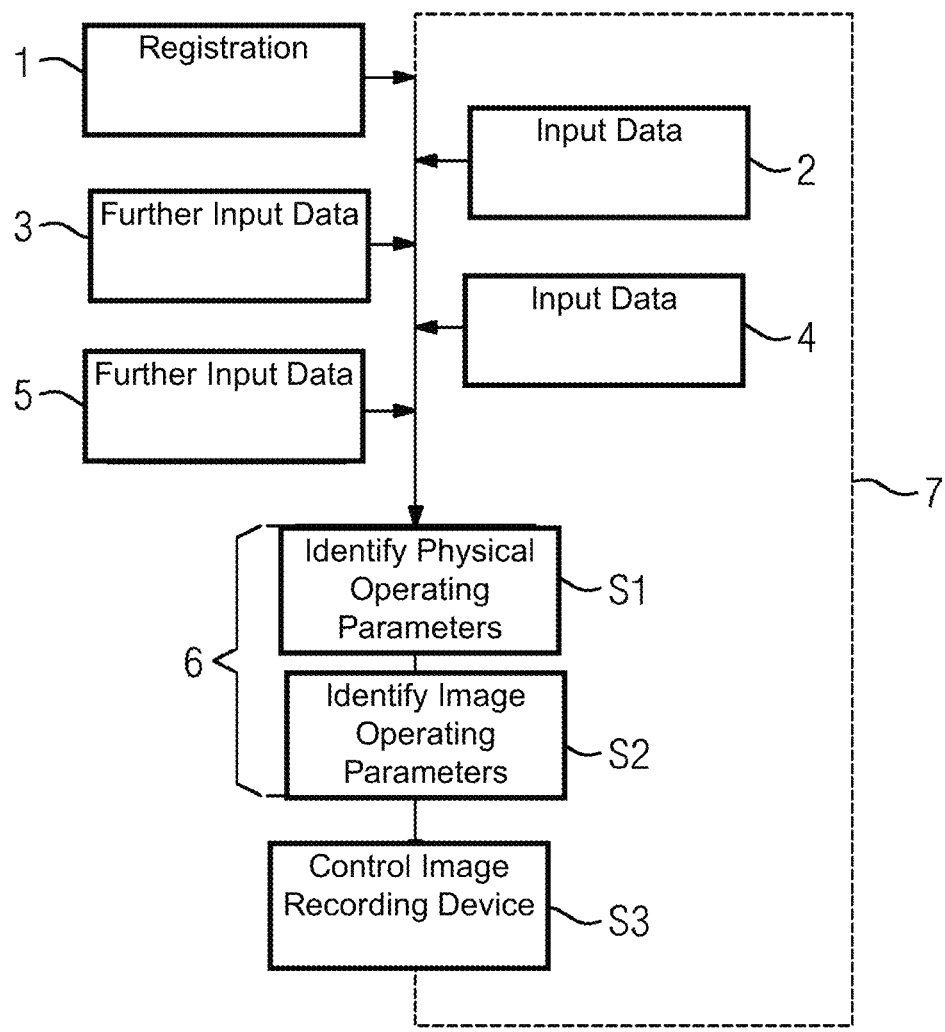
FIG. 1 shows a schematic sequence diagram of one embodiment of a method.

One embodiment of a procedure is explained in greater detail with reference to the sequence diagram in FIG. 1. The input information for the identification algorithm, which may also include at least one artificial intelligence algorithm, includes, for example, input data 2 to 5 in addition to the previously mentioned registration 1 of the patient, where the patient model (e.g., input data 2) will be explained in greater detail first.

In the exemplary embodiment described, use is made of an essentially generic patient model that is adapted to the current patient and registered with the coordinates system of the image recording device as a result of the registration 1. In this case, a patient model of the computed tomography type, which replicates all important organs and the vascular tree, and/or a vector-based simple patient model, which replicates the outlines of a generic patient and the location of all important organs relative to the outlines, may be used as a patient model. The registration data obtained in the context of the registration describes not only the location and position of the patient, but also further relevant properties thereof (e.g., extensions/outlines), such that both adaptation of the patient model to the current patient and, based on the registration, suitable positioning of the patient model relative to the coordinates system of the image recording device may be effected without difficulty by algorithms in the control device of the image recording device. The combination of patient model and registration described above represents a principle of the procedure described here.

Many different approaches and combinations of approaches may be used for the purpose of producing the registration 1. For example, a camera-based optical system replicates the patient on the patient couch of the image recording device and generates a correlation of the patient outline relative to the patient couch. As another example, an infrared-based system works in a similar way to the camera that measures in the visible range, but may measure through coverings in the same way as a terahertz camera. As other examples, an ultrasound-based recognition system with corresponding ultrasound sensors may be used, and/or a pressure-sensitive film, integrated into the patient couch, that may measure the main supporting points and correlate these with the patient model may be used. Supplementary information relating to the patient (e.g., inputs relating to the location of the patient on the patient couch and patient-specific patient data (e.g., height, age, gender, weight, etc.) may be used. This type of patient data may be retrieved from, for example, information systems (e.g., from a hospital information system (HIS) and/or a radiology information system (RIS)).

Further input data 3 describes the system state of the image recording device (e.g., the current recording geometry defined by the recording arrangement). In the case of the X-ray device, the positioning of the X-ray source and the X-ray detector may be described, for example, as a recording arrangement (e.g., that may be supported by a C-arm) relative to the patient couch. This may represent an important item of information in the context of the exemplary embodiments described since it is then possible, in conjunction with the patient model (e.g., input data 2, registration 1), which is present in the coordinates system of the image recording device and describes relevant organs/anatomical structures of the patient, to directly establish which part of the patient is situated in the field of view of the image recording device. This represents a clear indication of the image recording purpose and/or the organ of interest (OOI). The image recording purpose may be derived directly from the registration of the patient with the coordinates system of the image recording device (e.g., in combination with the patient model and/or further input data that describes the image recording purpose).

Further input data 5, relating to the image recording routine or specifically the image recording purpose, may again be retrieved from, for example, one of the information systems cited above. A corresponding combination of the knowledge relating to the part of the patient in the field of view (e.g., registration 1, input data 2, 3) with the further input data 5 relating to the image recording purpose results in particularly accurate knowledge with respect to the operating parameters that are expected to be required and the values thereof. For example, if the input data 5 specifies that a cardioangiography is to be performed, and if the part of the patient situated in the field of view of the image recording device suggests that the right-hand coronary artery is to be recorded, the background knowledge that the right-hand coronary artery moves more quickly than the left-hand coronary artery may be used to select, for example, correspondingly short pulses or a corresponding image frequency in order to minimize movement artifacts and optimize the temporal resolution.

With regard to the input data 3 (e.g., operating state of the image recording device), corresponding information is often already available or may easily be supplemented in the control device of the image recording device, as feedback from actuators that have been triggered and/or via corresponding sensor systems. The input data 3 may also include information relating to resources in use and optional and/or settable components (e.g., with regard to collimators and/or filters). Such input data 3 may also be derived from image data of the image recording device itself.

Also derivable from image data or retrievable from an information system is information relating to implants of the patient. This information may be identified as belonging to the input data 2. In one embodiment, when X-ray imaging is used as an imaging type, implants may have an influence due to attenuating properties, and therefore, operating parameters are configured to take the presence of these into account.

A further extremely useful item of input information is the input data 4, which relates to medical instruments (e.g., "devices") that are used, for example, on and/or in the patient during the image recording routine. Such medical instruments may also be associated with the image recording purpose and/or have an influence on the image recording. Therefore, knowledge of these may be extremely useful. Information about devices used may be identified by reading information media (e.g., bar codes) using a corresponding identification device. An image-based correlation of the instrument properties may optionally take place, possibly with the aid of segmentation algorithms. The input data 4 also includes properties that have been stored with respect to the medical instruments (e.g., the material), the geometrical extensions in at least one dimension, etc., where the properties may likewise be used during the identification of the operating parameters.

The performance of the identification algorithm 6 ultimately takes place in two acts S1 and S2. Physical operating parameters, which may also be referred to as image recording parameters and relate to the physical image recording routine, are identified first in the act S1. Image processing operating parameters (e.g., image evaluation parameters) are then identified as a function thereof in act S2. As mentioned above, the identification algorithm 6 may include at least one artificial intelligence algorithm. The algorithm is trained by training data, for example, that may be identified by logging during the use of image recording devices that operate based on measurement protocols. Artificial intelligence is suitable in the case of highly complex factual components, for example, while many of the facts described, as suggested by the description, may already be deduced without the use of artificial intelligence.

In specific exemplary embodiments, for example, operating parameters describing the X-ray dose and the X-ray spectrum may be identified as image recording parameters by identifying compositional information relating to the radiographed region based on the known part of the patient in the field of view and knowledge relating to implants if applicable. The compositional information is then used as a basis for selecting the corresponding operating parameters. Artificial intelligence approaches may also be used in this context. Optimization may take place with regard to the expected primary and scattered radiation components, for example. The knowledge relating to implants may also influence the superimposition of collimators and/or the use of filters to optimize the X-ray spectrum. With regard to the pulse length and/or the image recording frequency as operating parameters for example, information relating to the movement of the organ of interest (OOI) may be identified and evaluated accordingly. Depending on the selected physical operating parameters and the input data 2 to 5, image evaluation parameters are then identified in act S2 as operating parameters (e.g., the strength of the temporal and image-based noise suppression, the parameter describing management of contrast and dynamics, the spatial frequency-dependent image sharpness, etc.).

In one embodiment, in a further act of the identification algorithm 6 (omitted here for the sake of clarity), operating parameters relating to workflow instructions for output may also be identified as a further class of operating parameters. By such workflow instructions, these being generated automatically, the user may be informed of components/resources that should or should not be used (e.g., an antidiffusion grid), and/or minimization of a skin dose, etc. may be achieved by corresponding workflow instructions to the user.

In act S3, the identified operating parameters are then used to control the image recording device (e.g., therefore for image acquisition, image processing, image display, and image storage).

As indicated by the arrow 7, the described input data may be updated synchronously with the image (e.g., if the recording geometry and/or the position of the patient couch changes during an image sequence). This may be caused by the movement of a medical instrument that is to be tracked within the patient, for example. It is therefore possible for operating parameters that are always selected in the most optimal manner based on the current circumstances to be identified by the identification algorithm 6, which is then also performed synchronously with the image accordingly.

The operating parameters may also include positions that are to be automatically adopted by the patient couch, and therefore, as per the registration, the patient, and/or the recording arrangement (e.g., system positions), and the number thereof for consecutive image recordings by the image recording device. For example, the input data 2 to 5 may specify that a coronary examination is to take place (e.g., with specific imaging requirements), but may also describe the position, orientation, and size of the heart based on the patient model. It is possible therefrom to determine suitable recording geometries for examinations including a plurality of image recording routines, and describe, for example, patient couch positions and recording arrangement positions that may be adopted automatically (e.g., specific system positions) as operating parameters.

For example, the system positions in this case may be learned automatically during the daily clinical routine from training data describing examinations of the same type. As in other real application scenarios, it is possible to learn in a clinic-specific and/or user-specific manner, for example, and therefore to utilize the operating parameters that are locally and/or individually preferred accordingly.

Figure 2:
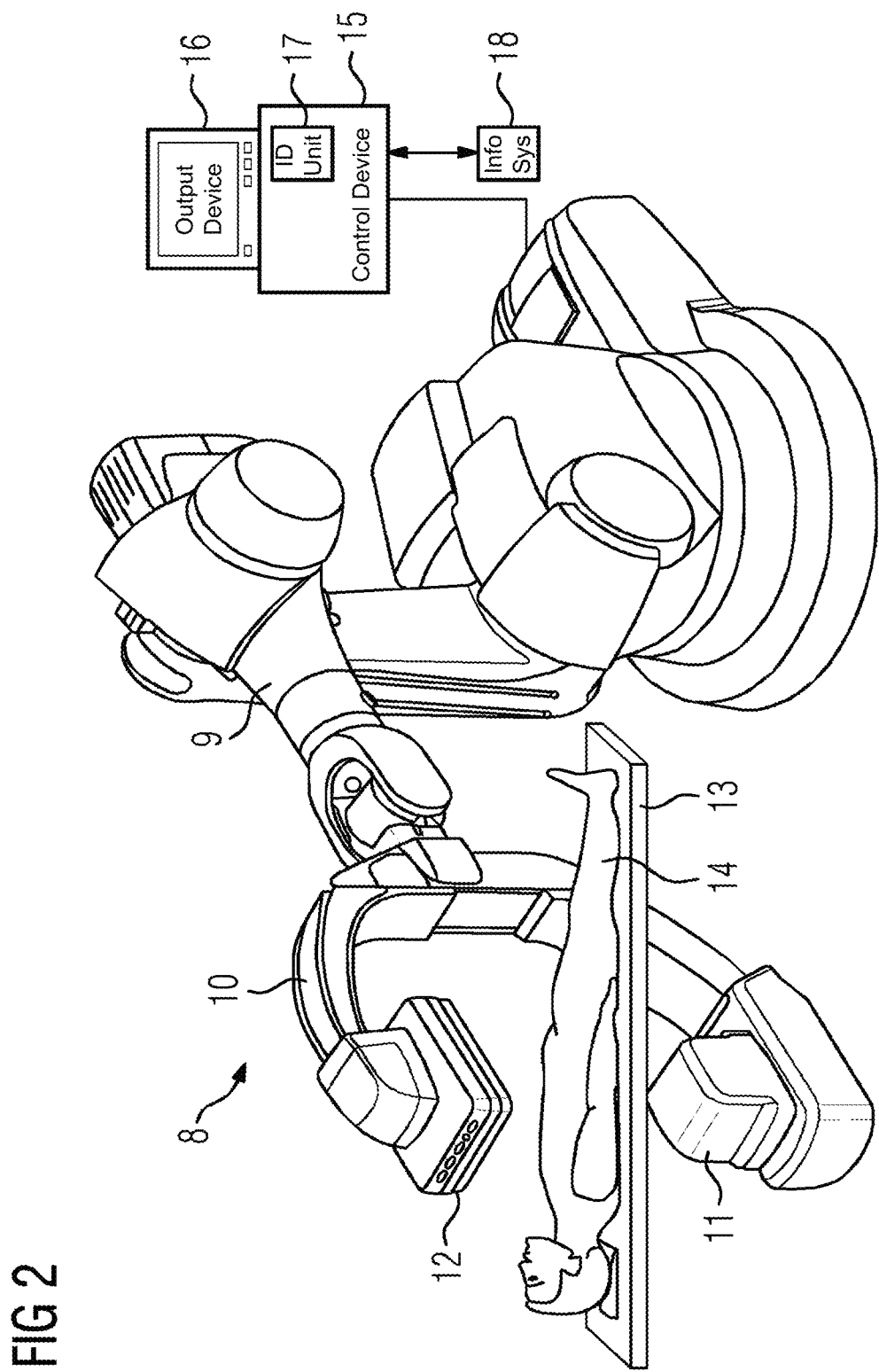
FIG. 2 shows one embodiment of an image recording device in the form of an X-ray device.

FIG. 2 shows an illustration of one embodiment of an image recording device 8 in the form of an interventional X-ray device (e.g., including a C-arm 10 that is mounted on a mobile robot arm 9 and on which are arranged an X-ray source 11 and an opposing X-ray detector 12 as a recording arrangement). It is thereby possible to realize various recording geometries in relation to a patient couch 13, which may likewise be configured to be mobile and on which the patient 14 to be examined and/or treated may be placed. The operation of the image recording device 8 is controlled in this case by a control device 15, which is also configured to perform the method according to one or more of the present embodiments.

The control device 15 may be assigned an output device 16 for outputting workflow instructions (e.g., a display screen and/or an acoustic output device). For the purpose of executing the identification algorithm 6, the control device 15 may have, for example, a corresponding identification unit 17 in addition to other functional units. The control device 15 may also be configured to communicate with external information systems 18.

Although the invention is illustrated and described in detail above by the exemplary embodiments, the invention is not restricted by the examples disclosed herein. Other variations may be derived therefrom by a person skilled in the art without departing from the scope of the invention.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a medical image recording device in the context of an image recording routine for a patient, the image recording routine serving an image recording purpose, wherein the image recording device is controlled based on operating parameters implemented by a controller of the image recording device, the method comprising:
identifying the operating parameters completely automatically by an identification algorithm from input data describing at least the patient in the form of a patient model, the image recording purpose, or a combination thereof, and from a registration of the patient with a coordinates system of the image recording device; and
controlling the image recording device using the identified operating parameters,
wherein an examination region that is to be recorded for the patient and the image recording purpose are derived by the registration.

2. The method of claim 1, further comprising identifying a workflow based on the registration of the patient with the coordinates system of the image recording device and based on the image recording purpose derived at least therefrom,
wherein the medical image recording device is configured to perform the identified workflow semiautomatically or automatically during the image recording routine for the patient.

3. The method of claim 1, wherein the identification algorithm comprises at least one artificial intelligence algorithm trained by of machine learning.

4. The method of claim 3, further comprising identifying training data for the artificial intelligence algorithm, the identifying of the training data comprising logging a user activity that comprises at least one individual parameter adaptation during the use of predefined measurement protocols with predefined operating parameters.

5. The method of claim 1, wherein the operating parameters comprise image recording parameters and at least one image evaluation parameter.

6. The method of claim 1, wherein at least the patient model that has been adapted to the current patient, and which describes a composition of the patient in a locally resolved manner, is used as the patient data describing the patient.

7. The method of claim 1, wherein the registration is effected using sensor data from at least one sensor directed at the patient, image data of the patient recorded by the image recording device, based on patient data retrieved from an information system, based on patient location data obtained from a patient couch of the image recording device, or any combination thereof.

8. The method of claim 7, wherein the patient model in use is adapted to the current patient based on registration data gathered during the registration, such that features contained in the patient model are localizable in the coordinates system of the image recording device.

9. The method of claim 1, further comprising retrieving input data describing the image recording purpose from an information system, deriving the input data from other input data, or a combination thereof.

10. The method of claim 9, wherein the other input data comprises data from a part of the patient that is positioned within the field of view of the image recording device.

11. The method of claim 1, wherein the input data comprises at least one item of instrument data describing a medical instrument that is used for the patient during the image recording routine.

12. The method of claim 11, wherein the instrument data is identified using an identification device that reads an information medium on the instrument, a packaging of the instrument, or on the instrument and the packaging of the instrument, from instrument data in an information system, by evaluating image data of the image recording device showing the instrument, the instrument data comprises at least one property that is relevant for the imaging type of the image recording device, or any combination thereof.

13. The method of claim 11, wherein the operating parameters identified by the identification algorithm include an operating parameter of the medical instrument that is used during the image recording routine.

14. The method of claim 1, wherein presence, positions, or the presence and the positions of components of the image recording device are identifiable from a state of actuators assigned thereto, by sensors assigned to the components, or from the state of the actuators and by the sensors.

15. The method of claim 1, wherein the input data is updated cyclically, in the event of change, or cyclically and in the event of change, and
wherein an adaptation of at least one of the operating parameters is effected based on the updated input data.

16. The method of claim 1, wherein at least one property of the recording region of the patient that is relevant for the imaging type used in the image recording device is identified by the identification algorithm and used to adapt at least one operating parameter.

17. The method of claim 1, wherein the operating parameters include an automatic output of at least one workflow instruction in relation to a resource to be used during the image recording, in order to minimize a negative effect on the patient, or in relation to the resource to be used during the image recording and in order to minimize the negative effect on the patient.

18. An image recording device comprising:
a recording arrangement; and
a controller configured to operate the recording arrangement in the context of an image recording routine for a patient, the image recording routine serving an image recording purpose, wherein the image recording device is controlled based on operating parameters implemented by the controller of the image recording device, the operation of the recording arrangement comprising:
identification of the operating parameters completely automatically by an identification algorithm from input data describing at least the patient in the form of a patient model, the image recording purpose, or a combination thereof, and from a registration of the patient with a coordinates system of the image recording device; and
control of the image recording device using the identified operating parameters,
wherein an examination region that is to be recorded for the patient and the image recording purpose are derived by the registration.

19. In a non-transitory computer-readable storage medium that stores instructions executable by one or more processors to operate a medical image recording device in the context of an image recording routine for a patient, the image recording routine serving an image recording purpose, wherein the image recording device is controlled based on operating parameters implemented by a controller of the image recording device, the instructions comprising:

identifying the operating parameters completely automatically by an identification algorithm from input data describing at least the patient in the form of a patient model, the image recording purpose, or a combination thereof, and from a registration of the patient with a coordinates system of the image recording device; and controlling the image recording device using the identified operating parameters, wherein an examination region that is to be recorded for the patient and the image.

* * * * *